(12) United States Patent
Yang-Yen

(10) Patent No.: US 12,064,466 B2
(45) Date of Patent: Aug. 20, 2024

(54) METHODS OF TREATING HYPERTRIGLYCERIDEMIA OR HYPERTRIGLYCERIDEMIA-RELATED DISEASES

(71) Applicant: Academia Sinica, Taipei (TW)

(72) Inventor: Hsin-Fang Yang-Yen, Taipei (TW)

(73) Assignee: Academia Sinica, Taipei (TW)

( * ) Notice: Subject to any disclaimer, the term of this patent is extended or adjusted under 35 U.S.C. 154(b) by 176 days.

(21) Appl. No.: 17/730,195

(22) Filed: Apr. 27, 2022

(65) Prior Publication Data

US 2022/0339245 A1  Oct. 27, 2022

Related U.S. Application Data

(60) Provisional application No. 63/180,425, filed on Apr. 27, 2021.

(51) Int. Cl.
*A61K 38/17* (2006.01)
*A61P 3/06* (2006.01)

(52) U.S. Cl.
CPC ............ *A61K 38/1709* (2013.01); *A61P 3/06* (2018.01)

(58) Field of Classification Search
CPC .............................. A61K 38/1709; A61P 3/06
See application file for complete search history.

(56) References Cited

U.S. PATENT DOCUMENTS

| | | | |
|---|---|---|---|
| 2002/0115153 A1* | 8/2002 | Lal et al. | C07K 14/47 |
| 2007/0160596 A1* | 7/2007 | Hoii et al. | C07K 14/4703 |

FOREIGN PATENT DOCUMENTS

| | | | |
|---|---|---|---|
| WO | WO2013151670 A1 | * | 10/2013 |
| WO | WO2016170176 A1 | * | 10/2016 |
| WO | WO2017168014 A1 | * | 10/2017 |
| WO | WO2017182634 A1 | * | 10/2017 |
| WO | WO2017191274 A2 | * | 11/2017 |
| WO | WO2018204534 A1 | * | 11/2018 |
| WO | WO2019046815 A1 | * | 3/2019 |
| WO | WO2019051424 A2 | * | 3/2019 |
| WO | WO2020051374 A1 | * | 3/2019 |
| WO | WO2019126574 A1 | * | 6/2019 |
| WO | WO2019173636 A1 | * | 9/2019 |
| WO | WO2020051374 A1 | * | 3/2020 |

OTHER PUBLICATIONS

At Work, Primary, secondary and tertiary prevention, 2015, 80: pp. 1-3 (Year: 2015).*

(Continued)

*Primary Examiner* — James H Alstrum-Acevedo
*Assistant Examiner* — Saleha Kuzniewski
(74) *Attorney, Agent, or Firm* — NZ Carr Law Office

(57) ABSTRACT

The present invention is directed to methods of treating hypertriglyceridemia or hypertriglyceridemia-related diseases in a subject by using recombinant PRAP1 polypeptides. According to some embodiments of the present disclosure, the subject is a human, in which the recombinant PRAP1 polypeptide comprises the amino acid sequence 100% identical to SEQ ID NO: 1 or 2. According to certain embodiments of the present disclosure, the subject is a mouse, in which the recombinant PRAP1 polypeptide comprises the amino acid sequence 100% identical to SEQ ID NO: 3 or 4.

8 Claims, 2 Drawing Sheets
Specification includes a Sequence Listing.

(56) References Cited

OTHER PUBLICATIONS

Rygiel et al., Hypertriglyceridemia—Common Causes, Prevention and treatment Strategies, 2018, Current Cardiology Reviews, 14: 67-76 (Year: 2018).*

Yuan et al., Hypertriglyceridemia: its etiology, effects and treatment, 2007, Canadian Medical Association, 176(8): 1113-1120 (Year: 2007).*

Gan et al., Hypertriglyceridemia-induced pancreatitis: A case-based review, World Journal of Gastroenterology, 12(44): 7197-7202 (Year: 2006).*

* cited by examiner (A)  (B)

SEQUENCE LISTING

```
<160> NUMBER OF SEQ ID NOS: 12

<210> SEQ ID NO 1
<211> LENGTH: 131
<212> TYPE: PRT
<213> ORGANISM: Artificial Sequence
<220> FEATURE:
<223> OTHER INFORMATION: synthesized_human rPRAP1 polyeptpdie-1

<400> SEQUENCE: 1

Val Pro Ala Pro Lys Val Pro Ile Lys Met Gln Val Lys His Trp Pro
1               5                   10                  15

Ser Glu Gln Asp Pro Glu Lys Ala Trp Gly Ala Arg Val Val Glu Pro
            20                  25                  30

Pro Glu Lys Asp Asp Gln Leu Val Val Leu Phe Pro Val Gln Lys Pro
        35                  40                  45
```

```
Lys Leu Leu Thr Thr Glu Glu Lys Pro Arg Gly Gln Gly Arg Gly Pro
 50                  55                  60

Ile Leu Pro Gly Thr Lys Ala Trp Met Glu Thr Glu Asp Thr Leu Gly
 65                  70                  75                  80

His Val Leu Ser Pro Glu Pro Asp His Asp Ser Leu Tyr His Pro Pro
                 85                  90                  95

Pro Glu Glu Asp Gln Gly Glu Glu Arg Pro Arg Leu Trp Val Met Pro
                100                 105                 110

Asn His Gln Val Leu Leu Gly Pro Glu Glu Asp Gln Asp His Ile Tyr
                115                 120                 125

His Pro Gln
        130

<210> SEQ ID NO 2
<211> LENGTH: 122
<212> TYPE: PRT
<213> ORGANISM: Artificial Sequence
<220> FEATURE:
<223> OTHER INFORMATION: synthesized_human rPRAP1 polyeptpdie-2

<400> SEQUENCE: 2

Val Pro Ala Pro Lys Val Pro Ile Lys Met Gln Val Lys His Trp Pro
 1               5                  10                  15

Ser Glu Gln Asp Pro Glu Lys Ala Trp Gly Ala Arg Val Val Glu Pro
                 20                  25                  30

Pro Glu Lys Asp Asp Gln Leu Val Val Leu Phe Pro Val Gln Lys Pro
                 35                  40                  45

Lys Leu Leu Thr Thr Glu Glu Lys Pro Arg Gly Thr Lys Ala Trp Met
 50                  55                  60

Glu Thr Glu Asp Thr Leu Gly His Val Leu Ser Pro Glu Pro Asp His
 65                  70                  75                  80

Asp Ser Leu Tyr His Pro Pro Glu Glu Asp Gln Gly Glu Glu Arg
                 85                  90                  95

Pro Arg Leu Trp Val Met Pro Asn His Gln Val Leu Leu Gly Pro Glu
                100                 105                 110

Glu Asp Gln Asp His Ile Tyr His Pro Gln
                115                 120

<210> SEQ ID NO 3
<211> LENGTH: 132
<212> TYPE: PRT
<213> ORGANISM: Artificial Sequence
<220> FEATURE:
<223> OTHER INFORMATION: synthesized_mouse rPRAP1 polyeptpdie-1

<400> SEQUENCE: 3

Ala Pro Ala His Gln Val Pro Val Lys Thr Lys Gly Lys His Val Phe
 1               5                  10                  15

Pro Glu Gln Glu Thr Glu Lys Val Gly Arg Val Trp Asp Thr Arg Ala
                 20                  25                  30

Leu Glu Pro Leu Glu Lys Asp Asn Gln Leu Gly Pro Leu Leu Pro Glu
                 35                  40                  45

Pro Lys Gln Lys Pro Ala Ala Glu Glu Lys Arg Pro Asp Ala Met
 50                  55                  60

Thr Trp Val Glu Thr Glu Asp Ile Leu Ser His Leu Arg Ser Pro Leu
 65                  70                  75                  80

Gln Gly Pro Glu Leu Asp Leu Asp Ser Ile Asp His Pro Met Ser Asp
                 85                  90                  95
```

Asp Val Gln Asp Glu Glu Val Pro Gln Ser Arg Pro Ile Leu Tyr Arg
                100                 105                 110

Gln Val Leu Gln Gly Pro Glu Asp Leu Asp His Leu Ala His Ser
            115                 120                 125

Met Glu Asp Ser
        130

<210> SEQ ID NO 4
<211> LENGTH: 129
<212> TYPE: PRT
<213> ORGANISM: Artificial Sequence
<220> FEATURE:
<223> OTHER INFORMATION: synthesized_mouse rPRAP1 polyeptpdie-2

<400> SEQUENCE: 4

Ala Pro Ala His Gln Val Pro Val Lys Thr Lys Gly Lys His Val Phe
1               5                   10                  15

Pro Glu Gln Glu Thr Glu Lys Val Trp Asp Thr Arg Ala Leu Glu Pro
            20                  25                  30

Leu Glu Lys Asp Asn Gln Leu Gly Pro Leu Leu Pro Glu Pro Lys Gln
        35                  40                  45

Lys Pro Ala Ala Ala Glu Glu Lys Arg Pro Asp Ala Met Thr Trp Val
    50                  55                  60

Glu Thr Glu Asp Ile Leu Ser His Leu Arg Ser Pro Leu Gln Gly Pro
65                  70                  75                  80

Glu Leu Asp Leu Asp Ser Ile Asp His Pro Met Ser Asp Val Gln
                85                  90                  95

Asp Glu Glu Val Pro Gln Ser Arg Pro Ile Leu Tyr Arg Gln Val Leu
                100                 105                 110

Gln Gly Pro Glu Glu Asp Leu Asp His Leu Ala His Ser Met Glu Asp
            115                 120                 125

Ser

<210> SEQ ID NO 5
<211> LENGTH: 151
<212> TYPE: PRT
<213> ORGANISM: Artificial Sequence
<220> FEATURE:
<223> OTHER INFORMATION: synthesized_human PRAP1_variant 1

<400> SEQUENCE: 5

Met Arg Arg Leu Leu Leu Val Thr Ser Leu Val Val Val Leu Leu Trp
1               5                   10                  15

Glu Ala Gly Ala Val Pro Ala Pro Lys Val Pro Ile Lys Met Gln Val
            20                  25                  30

Lys His Trp Pro Ser Glu Gln Asp Pro Glu Lys Ala Trp Gly Ala Arg
        35                  40                  45

Val Val Glu Pro Pro Gly Lys Asp Asp Gln Leu Val Val Leu Phe Pro
    50                  55                  60

Val Gln Lys Pro Lys Leu Leu Thr Thr Glu Glu Lys Pro Arg Gly Gln
65                  70                  75                  80

Gly Arg Gly Pro Ile Leu Pro Gly Thr Lys Ala Trp Met Glu Thr Glu
                85                  90                  95

Asp Thr Leu Gly His Val Leu Ser Pro Glu Pro Asp His Asp Ser Leu
                100                 105                 110

Tyr His Pro Pro Pro Glu Glu Asp Gln Gly Glu Glu Arg Pro Arg Leu
            115                 120                 125

```
Trp Val Met Pro Asn His Gln Val Leu Leu Gly Pro Glu Glu Asp Gln
        130                 135                 140

Asp His Ile Tyr His Pro Gln
145                 150

<210> SEQ ID NO 6
<211> LENGTH: 142
<212> TYPE: PRT
<213> ORGANISM: Artificial Sequence
<220> FEATURE:
<223> OTHER INFORMATION: synthesized_human PRAP1_variant 2

<400> SEQUENCE: 6

Met Arg Arg Leu Leu Leu Val Thr Ser Leu Val Val Leu Leu Trp
1               5                   10                  15

Glu Ala Gly Ala Val Pro Ala Pro Lys Val Pro Ile Lys Met Gln Val
                20                  25                  30

Lys His Trp Pro Ser Glu Gln Asp Pro Glu Lys Ala Trp Gly Ala Arg
            35                  40                  45

Val Val Glu Pro Pro Glu Lys Asp Asp Gln Leu Val Val Leu Phe Pro
50                  55                  60

Val Gln Lys Pro Lys Leu Leu Thr Thr Glu Glu Lys Pro Arg Gly Thr
65                  70                  75                  80

Lys Ala Trp Met Glu Thr Glu Asp Thr Leu Gly His Val Leu Ser Pro
                85                  90                  95

Glu Pro Asp His Asp Ser Leu Tyr His Pro Pro Glu Glu Asp Gln
                100                 105                 110

Gly Glu Glu Arg Pro Arg Leu Trp Val Met Pro Asn His Gln Val Leu
            115                 120                 125

Leu Gly Pro Glu Glu Asp Gln Asp His Ile Tyr His Pro Gln
        130                 135                 140

<210> SEQ ID NO 7
<211> LENGTH: 9
<212> TYPE: PRT
<213> ORGANISM: Artificial Sequence
<220> FEATURE:
<223> OTHER INFORMATION: synthesized_human PRAP1 variant

<400> SEQUENCE: 7

Gln Gly Arg Gly Pro Ile Leu Pro Gly
1               5

<210> SEQ ID NO 8
<211> LENGTH: 152
<212> TYPE: PRT
<213> ORGANISM: Artificial Sequence
<220> FEATURE:
<223> OTHER INFORMATION: synthesized_mouse PRAP1_isoform CRA a

<400> SEQUENCE: 8

Met Lys Arg Phe Leu Leu Ala Thr Cys Leu Val Ala Ala Leu Leu Trp
1               5                   10                  15

Glu Ala Gly Ala Ala Pro Ala His Gln Val Pro Val Lys Thr Lys Gly
                20                  25                  30

Lys His Val Phe Pro Glu Gln Glu Thr Glu Lys Val Gly Arg Val Trp
            35                  40                  45

Asp Thr Arg Ala Leu Glu Pro Leu Glu Lys Asp Asn Gln Leu Gly Pro
50                  55                  60
```

```
Leu Leu Pro Glu Pro Lys Gln Lys Pro Ala Ala Glu Glu Lys Arg
 65                  70                  75                  80

Pro Asp Ala Met Thr Trp Val Glu Thr Glu Asp Ile Leu Ser His Leu
                 85                  90                  95

Arg Ser Pro Leu Gln Gly Pro Glu Leu Asp Leu Asp Ser Ile Asp His
                100                 105                 110

Pro Met Ser Asp Asp Val Gln Asp Glu Glu Val Pro Gln Ser Arg Pro
                115                 120                 125

Ile Leu Tyr Arg Gln Val Leu Gln Gly Pro Glu Glu Asp Leu Asp His
            130                 135                 140

Leu Ala His Ser Met Glu Asp Ser
145                 150
```

<210> SEQ ID NO 9
<211> LENGTH: 149
<212> TYPE: PRT
<213> ORGANISM: Artificial Sequence
<220> FEATURE:
<223> OTHER INFORMATION: synthesized_mouse PRAP1_isoform CRA b

<400> SEQUENCE: 9

```
Met Lys Arg Phe Leu Leu Ala Thr Cys Leu Val Ala Ala Leu Leu Trp
 1               5                  10                  15

Glu Ala Gly Ala Pro Ala His Gln Val Pro Val Lys Thr Lys Gly
                 20                  25                  30

Lys His Val Phe Pro Glu Gln Glu Thr Glu Lys Val Trp Asp Thr Arg
             35                  40                  45

Ala Leu Glu Pro Leu Glu Lys Asp Asn Gln Leu Gly Pro Leu Leu Pro
         50                  55                  60

Glu Pro Lys Gln Lys Pro Ala Ala Glu Glu Lys Arg Pro Asp Ala
 65                  70                  75                  80

Met Thr Trp Val Glu Thr Glu Asp Ile Leu Ser His Leu Arg Ser Pro
                 85                  90                  95

Leu Gln Gly Pro Glu Leu Asp Leu Asp Ser Ile Asp His Pro Met Ser
                100                 105                 110

Asp Asp Val Gln Asp Glu Glu Val Pro Gln Ser Arg Pro Ile Leu Tyr
            115                 120                 125

Arg Gln Val Leu Gln Gly Pro Glu Glu Asp Leu Asp His Leu Ala His
        130                 135                 140

Ser Met Glu Asp Ser
145
```

<210> SEQ ID NO 10
<211> LENGTH: 20
<212> TYPE: PRT
<213> ORGANISM: Artificial Sequence
<220> FEATURE:
<223> OTHER INFORMATION: synthesized_human signal peptide

<400> SEQUENCE: 10

```
Met Arg Arg Leu Leu Leu Val Thr Ser Leu Val Val Leu Leu Trp
 1               5                  10                  15

Glu Ala Gly Ala
                 20
```

```
<210> SEQ ID NO 11
<211> LENGTH: 20
<212> TYPE: PRT
<213> ORGANISM: Artificial Sequence
<220> FEATURE:
<223> OTHER INFORMATION: synthesized_mouse signal peptide

<400> SEQUENCE: 11

Met Lys Arg Phe Leu Leu Ala Thr Cys Leu Val Ala Ala Leu Leu Trp
1               5                   10                  15

Glu Ala Gly Ala
            20

<210> SEQ ID NO 12
<211> LENGTH: 239
<212> TYPE: PRT
<213> ORGANISM: Artificial Sequence
<220> FEATURE:
<223> OTHER INFORMATION: synthesized-GST protein

<400> SEQUENCE: 12

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Glu Phe Pro Gly Arg Leu Glu Arg Pro His Arg Asp
225                 230                 235
```

METHODS OF TREATING HYPERTRIGLYCERIDEMIA OR HYPERTRIGLYCERIDEMIA-RELATED DISEASES

CROSS-REFERENCE TO RELATED APPLICATIONS

This application relates to and claims the benefit of U.S. Provisional Application No. 63/180,425, filed Apr. 27, 2021; the content of the application is incorporated herein by reference in its entirety.

BACKGROUND OF THE INVENTION

1. Field of the Invention

The present disclosure in general relates to the field of disease treatment. More particularly, the present disclosure relates to methods for treating hypertriglyceridemia or hypertriglyceridemia-related diseases by using recombinant proline-rich acidic protein 1 (PRAP1) polypeptides.

2. Description of Related Art

Patients with hypertriglyceridemia are predisposed to cardiovascular diseases and also show increased risk of acute pancreatitis. Lifestyle changes including weight loss, exercise and dietary modification are recommended as the first line for therapy of hypertriglyceridemia. However, drug therapy is often required. Many triglyceride (TG) lowering drugs have been reported, including niacin, fibrates, omega 3 fatty acids, volanesorsen, and lipoprotein lipase gene therapy (alipogene tiparvovec, Glybera). Other medicines primarily used to lower LDL-cholesterol (LDL-C), including statins, ezetimibe, inhibitors of proprotein convertase subtilisin/kexin type 9 (PCSK9 inhibitors), lomitapide and mipomersen, also exhibit effect on decreasing plasma TG levels. However, due to the limitations of drug efficacy, intolerance, and various side-effects, none of current known TG lowering medications alone provides a satisfactory effect.

In view of the foregoing, there exists in the related art a need for a novel agent and method for treating hypertriglyceridemia.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The first aspect of the disclosure is directed to a method of treating hypertriglyceridemia or a hypertriglyceridemia-related disease in a subject. The method comprises administering to the subject an effective amount of a recombinant PRAP1 polypeptide.

According to some embodiments of the present disclosure, the subject is a human, in which the recombinant PRAP1 polypeptide comprises an amino acid sequence 100% identical to SEQ ID NO: 1 or 2. In some preferred embodiments, the recombinant PRAP1 polypeptide consists of an amino acid sequence 100% identical to SEQ ID NO: 1 or 2.

According to certain embodiments of the present disclosure, the subject is a mouse, in which the recombinant PRAP1 polypeptide comprises an amino acid sequence 100% identical to SEQ ID NO: 3 or 4. In some preferred embodiments, the recombinant PRAP1 polypeptide consists of an amino acid sequence 100% identical to SEQ ID NO: 3 or 4.

Optionally, the recombinant PRAP1 polypeptide further comprises a signal peptide, which is disposed at and connected to the N-terminus of the TG-binding peptide. According to some embodiments, in the case when the TG-binding peptide has the amino acid sequence 100% identical to SEQ ID NO: 1 or 2, the signal peptide has an amino acid sequence 100% identical to SEQ ID NO: 10. According to alternative embodiments, in the case when the TG-binding peptide has the amino acid sequence 100% identical to SEQ ID NO: 3 or 4, the signal peptide has an amino acid sequence 100% identical to SEQ ID NO: 11.

Depending on desired purposes, the recombinant PRAP1 polypeptide may be administered to the subject via a suitable route, such as oral, intravenous, intra-arterial, subcutaneous or intraperitoneal administration. According to some embodiments, the recombinant PRAP1 polypeptide is orally administered to the subject every day for at least 7 days, for example, 7 or 14 days. According to alternative embodiments, the recombinant PRAP1 polypeptide is intravenously, intra-arterially, subcutaneously or intraperitoneally administered to the subject every day for 3 days.

The effective amount of the recombinant PRAP1 polypeptide administered to the subject is about 10 μg/Kg to 10 mg/Kg body weight per day; preferably, about 100 μg/Kg to 1,000 μg/Kg body weight per day; more preferably, about 500 μg/Kg to 1,000 μg/Kg body weight per day.

The hypertriglyceridemia-related disease is atherosclerosis, cardiovascular disease, or pancreatitis.

Also disclosed herein is a pharmaceutical composition for treating hypertriglyceridemia or hypertriglyceridemia-related diseases. The present pharmaceutical composition comprises a recombinant PRAP1 polypeptide and a pharmaceutically acceptable excipient, wherein the recombinant PRAP1 polypeptide comprises the amino acid sequence 100% identical to SEQ ID NO: 1, 2, 3 or 4.

Many of the attendant features and advantages of the present disclosure will become better understood with reference to the following detailed description considered in connection with the accompanying drawings.

BRIEF DESCRIPTION OF THE DRAWINGS

The present description will be better understood from the following detailed description read in light of the accompanying drawings, where:

FIG. 3A: C57BL/6 mice were fed a HFD and received oral gavage of vehicle alone (PBS) or rPRAP1 (10 mg/kg/day) for one (Panel (A)) or two weeks (Panel (B)), and their plasma TG levels were measured. FIG. 3B: Fecal lipid content (mg/g feces) of mice during the last 4 days of the 2-week treatment shown in FIG. 3A was measured. *, p<0.05; ***, p<0.001. n=20 for each treatment.

DETAILED DESCRIPTION OF THE INVENTION

Figure 1:
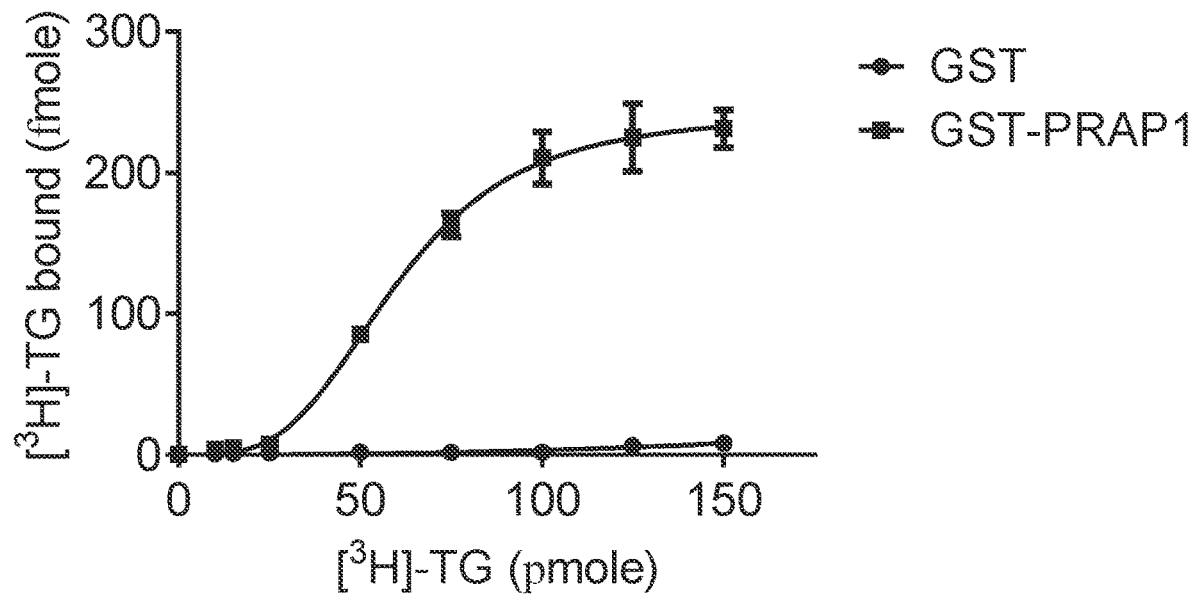
FIG. 1 depicts that PRAP1 directly binds to TG. $^3$H-labeled triglyceride ($[^3$H]-TG) binding curves of bacterially-produced glutathione S-transferase (GST) protein or GST fusion protein (a fusion protein comprising GST protein and wild-type PRAP1, GST-PRAP1). The binding experiment was done in triplicates, and results were presented as mean±SEM.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "polypeptide" refers to a polymer of amino acids without regard to the length of the polymer; thus, "peptides," "oligopeptides," and "proteins" are included within the definition of polypeptide and used interchangeably herein. This term also does not specify or exclude chemical or post-expression modifications of the polypeptides of the invention, although chemical or post-expression modifications of these polypeptides may be included or excluded as specific embodiments. Therefore, for example, modifications to polypeptides that include the covalent attachment of glycosyl groups, acetyl groups, phosphate groups, lipid groups and the like are expressly encompassed by the term polypeptide. Further, polypeptides with these modifications may be specified as individual species to be included or excluded from the present invention. Throughout the present disclosure, the positions of any specified amino acid residues within a polypeptide are numbered starting from the N terminus of the polypeptide. When amino acids are not designated as either D- or L-amino acids, the amino acid is either an L-amino acid or could be either a D- or L-amino acid, unless the context requires a particular isomer. Further, the notation used herein for the polypeptide amino acid residues are those abbreviations commonly used in the art.

The term "recombinant" as used herein refers to any cellular component produced in a cell (e.g., a prokaryotic or eukaryotic cell) as a result of genetic manipulation that is not naturally produced, or not normally produced in such amounts. With respect to a protein, the term "recombinant" means having an altered amino acid sequence as a result of the application of genetic engineering techniques to nucleic acids which encode the protein, and cells or organisms which express the protein. Specifically, the term "recombinant PRAP1 polypeptide" as used herein refers to a polypeptide having a modification (e.g., insertion, deletion or substitution of one or more amino acid residues) in its amino acid sequence as compared to that of a reference polypeptide (e.g., a wild-type PRAP1 polypeptide). According to some embodiments, the recombinant PRAP1 polypeptide has a signal peptide deletion as compared to the wild-type PRAP1 polypeptide.

As used herein, the term "signal peptide" (also known as "leader peptide" or "signal sequence") refers to an amino acid sequence located at the N terminus of a polypeptide that facilitates the secretion of the polypeptide from a mammalian cell. Signal peptides may be natural or synthetic, and may be heterologous or homologous to the polypeptide to which they are attached.

The term "administered", "administering" or "administration" are used interchangeably herein to refer a mode of delivery, including, without limitation, orally, intravenously, intraperitoneally, subcutaneously or intraarterially administering an agent (e.g., a recombinant PRAP1 polypeptide) of the present invention.

As used herein, the term "treat," "treating" and "treatment" are interchangeable, and encompasses partially or completely ameliorating, mitigating and/or managing a symptom, a secondary disorder or a condition associated with hypertriglyceridemia, in which decreasing the blood level of TG provides a benefit to the subject having or suspected of having such symptom, disorder or condition. The term "treating" as used herein refers to application or administration of one or more PRAP1 polypeptides of the present disclosure to a subject, who has a symptom, a secondary disorder or a condition associated with hypertriglyceridemia, with the purpose to partially or completely alleviate, ameliorate, relieve, delay onset of, inhibit progression of, reduce severity of, and/or reduce incidence of one or more symptoms, secondary disorders or features associated with hypertriglyceridemia. Symptoms, secondary disorders, and/or conditions associated with hypertriglyceridemia include, but are not limited to, atherosclerosis, cardiovascular disease and pancreatitis. Treatment may be administered to a subject who exhibits only early signs of such symptoms, disorder, and/or condition for the purpose of decreasing the risk of developing the symptoms, secondary disorders, and/ or conditions associated with hypertriglyceridemia. Treatment is generally "effective" if one or more symptoms or clinical markers are reduced as that term is defined herein. Alternatively, a treatment is "effective" if the progression of a symptom, disorder or condition is reduced or halted.

The term "effective amount" as referred to herein designate the quantity of a component which is sufficient to yield a desired response. For therapeutic purposes, the effective amount is also one in which any toxic or detrimental effects of the component are outweighed by the therapeutically beneficial effects. An effective amount of an agent is not required to cure a disease or condition but will provide a treatment for a disease or condition such that the disease or condition symptoms are ameliorated. The effective amount may be divided into one, two, or more doses in a suitable form to be administered at one, two or more times throughout a designated time period. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. Effective amount may be expressed, for example, in grams, milligrams or micrograms or as milligrams per kilogram of body weight (mg/Kg). Alternatively, the effective amount can be expressed in the concentration of the active component (e.g., the recombinant PRAP1 polypeptide of the present disclosure), such as molar concentration, mass concentration, volume concentration, molality, mole fraction, mass fraction and mixing ratio. Persons having ordinary skills could calculate the human equivalent dose (HED) for the medicament (such as the present recombinant PRAP1 polypeptide) based on the doses determined from animal models. For example, one may follow the guidance for industry published by US Food and Drug Administration (FDA) entitled "Estimating the Maximum Safe Starting Dose in Initial Clinical Trials for Therapeutics in Adult Healthy Volunteers" in estimating a maximum safe dosage for use in human subjects.

The phrase "pharmaceutically acceptable" refers to molecular entities and compositions that are "generally regarded as safe," e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "subject" refers to a mammal including the human species that is treatable with the recombinant PRAP1 polypeptide, the pharmaceutical composition and/or the method of the present invention. The term "subject" is intended to refer to both the male and female gender unless one gender is specifically indicated.

II. Description of the Invention

Proline-rich acidic protein 1 (PRAP1) is initially identified as a protein specifically expressed in the uterus during the mid to later stage of pregnancy, and accordingly named as pregnancy-specific uterine protein (PSUP). Later, PRAP1 is found to be abundantly expressed in the gut of both humans and mice, and is mainly in the small intestinal epithelium with a decreasing expression gradient along the duodenum-ileum axis. Very limited studies have been reported for PRAP1, and all studies reported so far in the literature suggest that PRAP1 has a role in embryo implantation, cell growth or death regulation. However, the underlying mechanism and its molecular function is not clear.

The present disclosure is based, at least in part, on the discovery that PRAP1 is capable of binding to TG, and enhancing the exclusion of TG thereby reducing lipid absorption in the subject. Accordingly, PRAP1 may serve as a potential agent to treat TG-associated diseases and/or conditions, e.g., hypertriglyceridemia, atherosclerosis, cardiovascular disease and/or pancreatitis.

(II-1) Recombinant Polypeptides and Pharmaceutical Composition Comprising the Same The first aspect of the present disclosure is directed to a recombinant PRAP1 polypeptide, in which compared to a wild-type (WT) PRAP1 polypeptide, the signal peptide (i.e., N-terminal 20 amino acid residues) is deleted in the recombinant PRPA1. According to some embodiments of the present disclosure, the recombinant PRAP1 polypeptide comprises a TG-binding peptide having an amino acid sequence 100% identical to SEQ ID NO: 1, 2, 3 or 4. According to certain preferred embodiments, the recombinant PRAP1 polypeptide consists of the TG-binding peptide of SEQ ID NO: 1, 2, 3 or 4.

Optionally, the recombinant PRAP1 polypeptide further comprises a signal peptide disposed at and connected to the N-terminus of the TG-binding peptide. According to some embodiments, in the case when the TG-binding peptide has the amino acid sequence of SEQ ID NO: 1 or 2, the signal peptide has an amino acid sequence 100% identical to SEQ ID NO: 10. According to some alternative embodiments, in the case when the TG-binding peptide has the amino acid sequence of SEQ ID NO: 3 or 4, the signal peptide has an amino acid sequence 100% identical to SEQ ID NO: 11.

Optionally, the recombinant PRAP1 polypeptide further comprises a protein tag linked to the N- or C-terminus of the TG-binding peptide. Depending on desired purposes, the protein tag may be an affinity tag that facilitates the purification of the recombinant PRAP1 polypeptide by using an affinity technique; examples of the affinity tag suitable to be linked to the present TG-binding peptide include, but are not limited to, GST, chitin-binding protein (CBP), maltose-binding protein (MBP), streptavidin-binding protein (SBP), calmodulin-binding protein, cellulose-binding protein, polyhistidine (poly-His) tag, polyarginine (poly-Arg) Tag, FLAG tag, myc tag, ALFA tag, E tag, HA tag, NE tag, T7 tag, and V5 tag. Alternately, the protein tag may be a solubilization tag to assist in the proper folding of the recombinant PARA1 polypeptide; for example, thioredoxin (TRX). Some affinity tags have dual role as an affinity tag and a solubilization agent, such as MBP, and GST. According to some exemplary embodiments, the recombinant PRAP1 polypeptide comprises a TG-binding peptide and a GST protein linked to the C-terminus of the TG-binding peptide. In these embodiments, the GST protein comprises the amino acid sequence of SEQ ID NO: 12.

Depending on desired purposes, the recombinant PRAP1 polypeptide of the present disclosure may be modified by an acetyl group (i.e., N-terminal acetylation), a phosphate group (i.e., phosphorylation), and/or a polyethylene glycol (PEG, i.e., PEGylation) thereby improving the stability, cellular process, bio-distribution and/or solubility of the recombinant polypeptide. Additionally or alternatively, the C-terminus of the recombinant RPAP1 polypeptide of the present disclosure may be amidated for the purpose of preventing enzyme degradation.

The present recombinant PRAP1 polypeptide may be produced by conventional recombinant technology. For example, a nucleic acid comprising a coding sequence for the recombinant PRAP1 polypeptide may be prepared using PCR techniques, or any other method or procedure known to one skilled in the art. The nucleic acid molecules thus obtained may be inserted into a suitable expression vector to enable the expression of the encoded recombinant protein in a suitable host cell. In some embodiments, the expression vector may include additional sequences, which render this vector suitable for replication and integration in prokaryotes or eukaryotes. Alternatively or additionally, the expression vector may comprise transcription and translation initiation sequences (e.g., promoters or enhancers), and transcription and translation terminators (e.g., polyadenylation signals). Exemplary expression vectors include, but are not limited to, bacterial expression vector, yeast expression vector, baculoviral expression vector, and mammalian expression vector. Any of the nucleic acids coding for the present recombinant PRAP1 polypeptide, a vector (such as an expression vector) comprising the nucleic acid, and host cells comprising the vector are also within the scope of the present disclosure.

A variety of prokaryotic or eukaryotic cells can be used as the host-expression system to express the present recombinant PRAP1 polypeptide. Examples of the expression systems include, but are not limited to, microorganisms, such as bacteria, yeast, plant cell, eukaryotic cell (e.g., mammalian cell or CHO cell), etc. Methods for transducing the expression vector into the host-expression system are known by a skilled artisan, e.g., stable or transient transfection, lipofection, electroporation and infection with recombinant viral vectors.

Also disclosed herein is a pharmaceutical composition for treating hypertriglyceridemia or hypertriglyceridemia-related diseases in a subject. The pharmaceutical composition comprises a recombinant PRAP1 polypeptide of the present disclosure, and a pharmaceutically acceptable excipient. As described above, the recombinant PRAP1 polypeptide may comprise the amino acid sequence 100% identical to any of SEQ ID NO: 1, 2, 3 or 4.

The pharmaceutical composition may comprise different types of excipients depending on the intended routes of administration. The present composition may be administered intravenously, subcutaneously, intraarterially, intraperitoneally or orally, in any suitable forms such as solutions, injections, and etc.

In some embodiments, the pharmaceutical compositions of the present disclosure are liquid dosage forms for oral administration. The liquid formulation may include a buffering agent to maintain a desired pH. The liquid dosage formulations may also be filled into soft gelatin capsules. For example, the liquid may include a solution, suspension, emulsion, micro-emulsion, precipitate or any desired liquid media carrying the recombinant polypeptide as described above, or a pharmaceutically acceptable derivative, salt or solvate thereof, or a combination thereof.

In some embodiments, the pharmaceutical compositions of this disclosure are formulations suitable for parenteral administration, such as administration by injection, which includes, but is not limited to, intravenous, intraarterial, subcutaneous and intraperitoneal injection. In general, the recombinant polypeptide may be in the form of a pyrogen-free, parenterally acceptable aqueous solution. The preparation of such parenterally acceptable polypeptide solutions, having due regard to pH, isotonicity, stability, and the like, is within the skill in the art. A preferred pharmaceutical composition for intravenous, intraarterial, subcutaneous or intraperitoneal injection should contain, in addition to the present recombinant PRAP1 polypeptide, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the invention may also contain stabilizers, preservatives, buffers, antioxidants, or other additives known to those of skill in the art.

(II-2) Methods of Treating Hypertriglyceridemia or Hypertriglyceridemia-Related Diseases Another aspect of the present disclosure pertains to a method of treating hypertriglyceridemia or a hypertriglyceridemia-related disease in a subject by using the recombinant PRAP1 polypeptide or the pharmaceutical composition in accordance with any embodiment of the present disclosure.

According to some working examples of the present disclosure, the recombinant PRAP1 polypeptide may be administered to the subject via oral or parenteral route, e.g., intravenous, intra-arterial, subcutaneous or intraperitoneal administration.

Two isoforms of PRAP1 polypeptide are identified in mouse due to the process of alternative splicing, including isoform CRA a (GenBank accession number: EDL17907; SEQ ID NO: 8) and isoform CRA b (GenBank accession number: EDL17908; SEQ ID NO: 9), in which the amino acid sequence "GRV" is present at positions 45-47 of the amino acid sequence of isoform CRA a (having 152 amino acid residues in length), and is absent in the amino acid sequence of isoform CRA b (having 149 amino acid residues in length). According to certain embodiments, the subject is a mouse, in which a recombinant PRAP1 polypeptide having the amino acid sequence of SEQ ID NO: 8 or 9 is administered to the subject so as to decrease the level of TG in the blood of the subject, and/or alleviate or ameliorate the symptoms associated with the hypertriglyceridemia-related disease. According to some preferred embodiments, a recombinant PRAP1 polypeptide having the amino acid sequence of SEQ ID NO: 3 (having N-terminal 20 amino acid residues deleted as compared to the WT PRAP1 polypeptide of SEQ ID NO: 8) or SEQ ID NO: 4 (having N-terminal 20 amino acid residues deleted as compared to the WT PRAP1 polypeptide of SEQ ID NO: 9) is administered to the subject so as to achieve the therapeutic effect.

The effective amount of the recombinant PRAP1 polypeptide may vary with many factors, such as the physical condition of the patient (e.g., the patient's body mass, age, or gender), the type of mammal or animal being treated, the duration of the treatment, and the nature of concurrent therapy (if any).

According to some embodiments of the present disclosure, to elicit a therapeutic effect in the mouse, the recombinant PRAP1 polypeptide is administered to the subject in the amount of about 100 µg/Kg to 100 mg/Kg body weight per dose; for example, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, or 990 µg/Kg body weight per dose; or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 mg/Kg body weight per dose; preferably, about 1 to 10 mg/Kg body weight per dose; more preferably, about 5 to 10 mg/Kg body weight per dose. In some exemplary embodiments, the recombinant PRAP1 polypeptide is intraperitoneally administered to the subject in the amount of 7 mg/Kg per day for 3 consecutive days. In alternative embodiments, the recombinant PRAP1 polypeptide is orally administered to the subject in the amount of 10 mg/Kg per day for at least 7 days, e.g., 7, 8, 9, 10, 11, 12, 13, 14, 15, 16, 17, 18, 19, 20 or more days. According to one working example, 10 mg/Kg of the recombinant PRAP1 polypeptide is orally administered to the subject for 7 days to produce a therapeutic effect in the subject. According to another working example, 10 mg/Kg of the recombinant PRAP1 polypeptide is orally administered to the subject for 14 days.

Similar to the PRAP1 polypeptide in mouse, two transcript variants of PRAP1 polypeptide are identified in human due to alternative splicing, including human PRAP1 transcript variant 1 (GenBank accession number: NP_660203; SEQ ID NO: 5), and human PRAP1 transcript variant 2 (GenBank accession number: NP_001138673; SEQ ID NO: 6), in which the amino acid sequence "QGRG-PILPG" (SEQ ID NO: 7) is present at positions 80-88 of the amino acid sequence of transcript variant 1 (having 151 amino acid residues in length), and is absent in the amino acid sequence of transcript variant 2 (having 142 amino acid residues in length). According to some embodiments, the subject is a human, in which a recombinant PRAP1 polypeptide having the amino acid sequence of SEQ ID NO: 5 or 6 is administered to the subject so as to decrease the level of TG in the blood of the subject, and/or alleviate or ameliorate the symptoms associated with the hypertriglyceridemia-related disease. According to some preferred embodiments, a recombinant PRAP1 polypeptide having the amino acid sequence of SEQ ID NO: 1 (having N-terminal 20 amino acid residues deleted as compared to the WT PRAP1 polypeptide of SEQ ID NO: 5) or SEQ ID NO: 2 (having N-terminal 20 amino acid residues deleted as compared to the WT PRAP1 polypeptide of SEQ ID NO: 6) is administered to the subject so as to produce the therapeutic effect in the subject.

A skilled artisan could calculate the human equivalent dose (HED) of the recombinant PRAP1 polypeptide or pharmaceutical composition, based on the doses determined from animal models. Accordingly, the HED of the recombinant PRAP1 polypeptide or pharmaceutical composition is about 10 µg/Kg to 10 mg/Kg body weight per dose for human; in other words, the effective HED of the present polypeptide may be any of, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980 or 990 µg/Kg body weight per dose for human; or 1, 2, 3, 4, 5, 6, 7, 8, 9 or 10 mg/Kg body weight per dose for human. Preferably, the HED of the recombinant PRAP1 polypeptide or pharmaceutical composition is about 100 µg/Kg to 1,000 µg/Kg body weight per day. More preferably, the HED of the recombinant PRAP1 polypeptide or pharmaceutical composition is about 500 µg/Kg to 1,000 µg/Kg body weight per day.

As would be appreciated, the present method can be applied to the subject, alone or in combination with additional therapies that have some beneficial effects on the treatment of hypertriglyceridemia. Depending on the intended/therapeutic purpose, the present method can be applied to the subject before, during, or after the administration of the additional therapies.

The subject treatable with the present recombinant PRAP1 polypeptide, pharmaceutical composition, and/or method is a mammal, for example, a human, mouse, monkey, rat, cat, dog, sheep, goat, or rabbit. Preferably, the subject is a human.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE

Materials and Methods

Production and Purification of Recombinant Mouse PRAP1 (rPRAP1) Polypeptide from Bacteria pGEX4T-1-PRAP1ΔN20 is a bacterial expression vector that directs the synthesis of a mouse PRAP1 without the N-terminal 20-aa signal peptide (PRAP1ΔN20) and having a glutathione S-transferase (GST) protein fused to its C-terminus. The thus-produced polypeptide comprised a TG-binding peptide of SEQ ID NO: 3, and a GST protein of SEQ ID NO: 12 linked to the C-terminus of the TG-binding peptide. The recombinant rPRAP1was purified with glutathione SEPHAROSE® 4B beads, and digested with thrombin to remove the GST portion, followed by inactivation of thrombin by adding protease inhibitor to a final concentration of 1 mM. Purified rPRAP1 was dialyzed in PBS.

Lipid Binding Assay

Binding of [$^3$H]-TG (triolein, [9,10-$^3$H(N)]) to rPRAP1 proteins was carried out as follows. Briefly, approximately 0.7 µg of GST or GST-PRAP1 proteins bound to glutathione SEPHAROSE® 4B beads were washed with buffer A (50 mM Tris-HCl pH 7.4 and 150 mM NaCl) three times and then re-suspended in 100 µL of buffer A containing the indicated amounts of [$^3$H]-TG. After 4 hour incubation at room temperature (RT), beads were washed three times with 800 μL of buffer A by centrifugation, and resuspended in 500 μL of buffer E (10 mM Tris HCl pH 7.4, 150 mM NaCl, 1 mM EDTA, and 1% TRITON™ X-100), and assayed for retained radioactivity using a scintillation counter.

Animal Study

C57BL/6 mice (male, 8-week old) were housed in a room with a 12 hour light/dark cycle (lights on at 7:00 A.M.) with ad libitum access to food (HFD, 58Y1-60% energy from fat, Test Diet; the ingredients were summarized in Table 1) and water. For the purpose of evaluating the effect of rPRAP1 on TG level in HFD-fed mice, rPRAP1 (7 mg/Kg/day) was intraperitoneally administered to the mice for 3 consecutive days; alternatively, rPRAP1 (10 mg/Kg/day) was orally administered to the mice for one or two weeks. All animal experiments were performed in accordance with the guidelines set by Academia Sinica Institutional Animal Care and Utilization Committee.

TABLE 1

Ingredients of HFD

| Ingredient | % weight/volume |
| --- | --- |
| lard | 31.66 |
| casein - vitamin tested | 25.85 |
| maltodextrin | 16.15 |
| sucrose | 8.85 |
| powdered cellulose | 6.46 |
| soybean oil | 3.23 |
| potassium citrate, tribasic monohydrate | 2.13 |
| calcium phosphate | 1.68 |
| dio mineral mix | 1.29 |
| AIN-76A vitamin mix* | 1.29 |
| calcium carbonate | 0.71 |
| l-cystine | 0.39 |
| choline bitartrate | 0.26 |

*AIN-76A vitamin mix included 0.6 gm of tiamine hydrochloride, 0.6 gm of riboflavin, 0.7 gm of pyridoxine hydrochloride. 3.0 gm of nicotinic acid, 1.6 gm of D-calcium pantothenate, 0.2 gm of folic acid, 0.02 gm of D-biotin, 0.001 gm of vitamin B12, 1.6 gm of vitamin A, 20.0 gm of DL-a-tocopherol acetate, 0.25 gm of cholecalciferol, 0.05 gm of menaquinone, and 971.38 gm of sucrose.

Measurements of Plasma Levels of Triglyceride

Plasma were collected from mice to be measured by standard methods, and the amounts of triglycerides were determined enzymatically using commercial kits.

Determination of Fecal Lipid Content

Feces over 4 days were collected from individually-housed mice that had been fed a HFD for 2 weeks.

Statistics

Statistical analysis was performed with t-test for comparison between two groups.

Example 1 Effect of rPRAP1 on Treating Hypertriglyceridemia

For the purpose of examining the TG-binding activity of PRAP1, GST or GST-PRAP1 polypeptide was mixed with $^3$H-labeled TG ([$^3$H]-TG) followed by the analysis of scintillation counter as described in Materials and Methods. The data of FIG. 1 demonstrated the direct binding of PRAP1 to TG.

Figure 2:
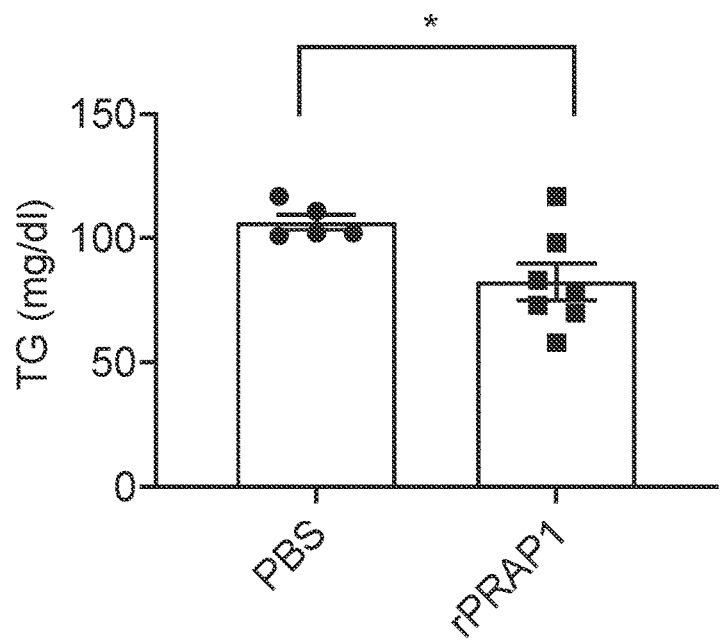
FIG. 2 depicts that intraperitoneal injection of the recombinant PRAP1 polypeptide (rPRAP1) decreased plasma levels of TG. C57BL/6 mice fed a high fat diet (HFD) were intraperitoneally injected with recombinant mouse PRAP1 polypeptide (rPRAP1, 7 mg/kg/day) or vehicle alone (phosphate buffered saline (PBS)) for 3 consecutive days. On the last injection day, plasma was collected and analyzed for TG levels. *, p<0.05, n=5-7 for each treatment.
Figure 3A:
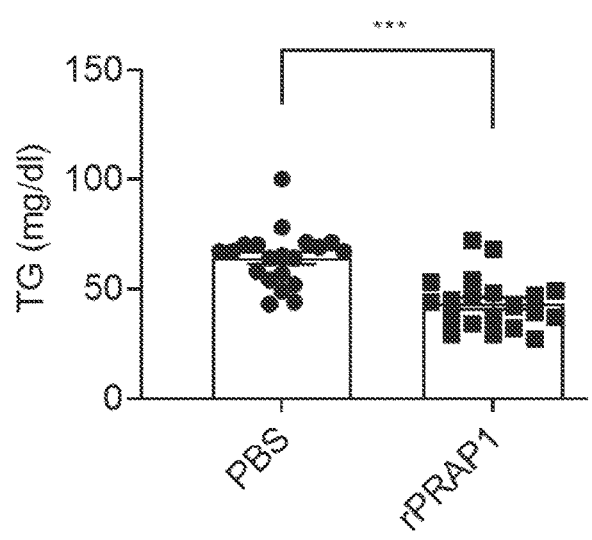
FIGS. 3A and 3B respectively depict that oral administration of the recombinant PRAP1 polypeptide decreased plasma levels of TG and increased fecal lipid excretion.
Figure 3A:
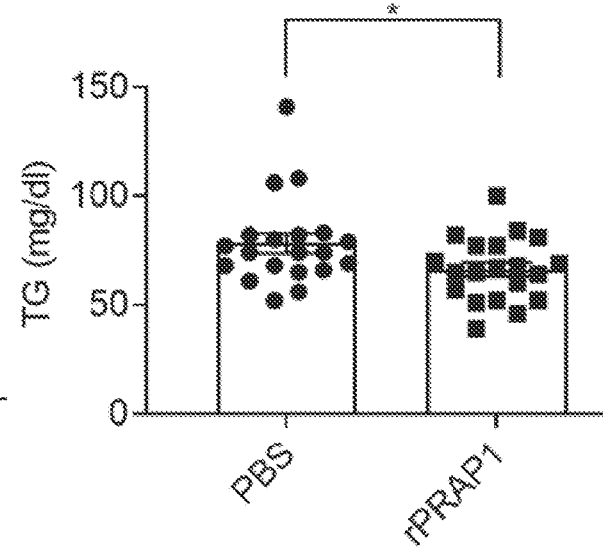
Figure 3B:
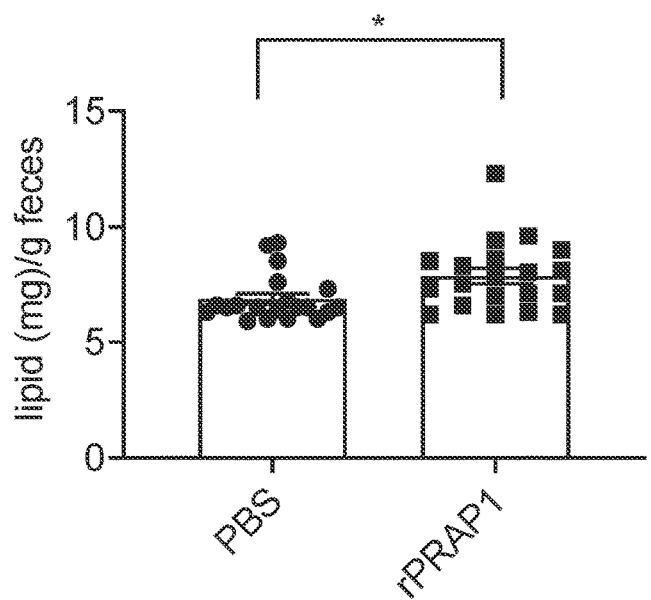

Then, C57BL/6 mice fed with HFD were used as an animal model to evaluate whether the administration of PRAP1 polypeptide may complex with TG, thereby improving the exclusion of TG and reducing lipid absorption. rPRAP1 (7 mg/Kg/day) was intraperitoneally administered to the mice for 3 consecutive days. As the data depicted in FIG. 2, compared to the control group (i.e., PBS-treated group), the administration of rPRAP1 significantly decreased plasma TG levels in mice. The results of FIG. 3 further confirmed that oral administration of rPRAP1 would exhibit a similar lipid-lowering effect, in which oral administration of rPRAP1 (10 mg/Kg/day) for one week (Panel (A) of FIG. 3A) or two weeks (Panel (B) of FIG. 3A) not only significantly decreased plasma TG levels in mice, and but also significantly increased lipid excretion in feces of mice (FIG. 3B).

These data suggested that the recombinant PRAP1 polypeptide (i.e., rPRAP1) may provide a potential means to treat hypertriglyceridemia or hypertriglyceridemia-related diseases via decreasing plasma TG levels in the subject and increasing lipid excretion in feces.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method of treating hypertriglyceridemia or a hypertriglyceridemia-related disease in a subject, comprising administering to the subject a recombinant proline-rich acidic protein 1 (PRAP1) polypeptide, wherein the subject is a human, and the recombinant PRAP1 polypeptide comprises an amino acid sequence 100% identical to SEQ ID NO: 1 or 2.

2. The method of claim 1, wherein the recombinant PRAP1 polypeptide is administered to the subject via oral, intravenous, subcutaneous, intra-arterial or intraperitoneal injection.

3. The method of claim 2, wherein the recombinant PRAP1 polypeptide is orally administered to the subject every day for at least 7 days.

4. The method of claim 2, wherein the recombinant PRAP1 polypeptide is intravenously, intra-arterially, subcutaneously or intraperitoneally administered to the subject every day for 3 days.

5. The method of claim 1, wherein the effective amount is about 10 µg/Kg to 10 mg/Kg body weight per day.

6. The method of claim 5, wherein the effective amount is about 100 µg/Kg to 1,000 µg/Kg body weight per day.

7. The method of claim 6, wherein the effective amount is about 500 µg/Kg to 1,000 µg/Kg body weight per day.

8. The method of claim 1, wherein the hypertriglyceridemia-related disease is atherosclerosis, cardiovascular disease, or pancreatitis.

* * * * *